United States Patent
Imamura et al.

(10) Patent No.: US 7,741,078 B2
(45) Date of Patent: Jun. 22, 2010

(54) HEPARIN-BINDING PROTEIN MODIFIED WITH HEPARAN SULFATE SUGAR CHAINS, PROCESS FOR PRODUCING THE SAME AND PHARMACEUTICAL COMPOSITIONS CONTAINING THE SAME

(75) Inventors: Toru Imamura, Tsukuba (JP); Masahiro Asada, Tsukuba (JP); Masashi Suzuki, Tsukuba (JP)

(73) Assignee: National Institute of Advanced Science and Technology, Tokyo (JP)

( * ) Notice: Subject to any disclaimer, the term of this patent is extended or adjusted under 35 U.S.C. 154(b) by 641 days.

(21) Appl. No.: 11/547,346

(22) PCT Filed: Mar. 31, 2005

(86) PCT No.: PCT/JP2005/006364

§ 371 (c)(1),
(2), (4) Date: Jan. 19, 2007

(87) PCT Pub. No.: WO2005/095600

PCT Pub. Date: Oct. 13, 2005

(65) Prior Publication Data

US 2008/0119403 A1    May 22, 2008

(30) Foreign Application Priority Data

Mar. 31, 2004    (JP)    ............... 2004-108570

(51) Int. Cl.
*C12N 15/12*    (2006.01)
*C12N 1/00*    (2006.01)
*C12P 21/02*    (2006.01)

(52) U.S. Cl. ............... 435/69.7; 536/23.4; 536/23.5

(58) Field of Classification Search ............... None
See application file for complete search history.

(56) References Cited

U.S. PATENT DOCUMENTS 5,486,599 A * 1/1996 Saunders et al. ............ 530/395
2003/0100492 A1 * 5/2003 Yayon ............... 514/12

2006/0079451 A1    4/2006 Imamura et al.

FOREIGN PATENT DOCUMENTS

JP    11-137255    5/1999
JP    11-137255 A    5/1999

OTHER PUBLICATIONS

International Preliminary Report on Patentability for International application No. PCT/JP2005/006364 issued Oct. 19, 2006.
International Search Report for International Application PCT/JP2005/006364 mailed Jun. 7, 2005.
M. Asada et al., Modification of FGF-1, preferentially with heparan sulfate but not chondroitin sulfate, Seikagaku, 76 (8), Aug. 25, 2004, p. 1006.
A. Yoneda et al., Engineering of an FGF-proteoglycan fusion protein with heparin-independent, mitogenic activity, Nat Biotechnol, 18(6), 2000, pp. 641 to 644.
Examination Report for 0B0621466.2, dated Oct. 22, 2007.
Office Action No. 652525 issued on Japanese Patent application No. 2004-108570, mailed Oct. 28, 2008.
Office Action No. 130437 issued on Japanese Patent Application No. 2004-108570, mailed Mar. 3, 2009.
Office Acton issued on UK Patent Application No. 0621466.2 on Jun. 27, 2008.
Office Action issued on UK Patent Application No. 0621466.2 on Sep. 12, 2008.
Office Action issued on UK Patent Application No. 0621466.2 on Oct. 2, 2008.

* cited by examiner

*Primary Examiner*—David A Saunders
(74) *Attorney, Agent, or Firm*—Hogan & Hartson LLP

(57) ABSTRACT

A heparin-binding protein having covalently bonded heparan sulfate sugar chains within its molecule is produced by ligating a cDNA encoding a peptide which can be modified with heparan sulfate sugar chains selectively to a cDNA encoding a heparin-binding protein and producing in an animal cell the gene product of the resultant ligated cDNA. This heparan sulfate sugar chain-modified heparin-binding protein is functionalized by covalently bonding thereto glycosaminoglycan sugar chains containing little chondroitin sulfate. For example, this heparin-binding protein is excellent in stabilities, such as thermostability, acid resistance, alkali resistance and in vivo stability. Further, the heparan sulfate sugar chain-modified heparin-binding protein is effective in cell proliferation and tissue regeneration, and has effect of regulating the physiological functions of FGFs. Thus, this heparin-binding protein is extremely useful as a medicine for preventing or treating various FGF-related diseases.

4 Claims, 2 Drawing Sheets

HEPARIN-BINDING PROTEIN MODIFIED WITH HEPARAN SULFATE SUGAR CHAINS, PROCESS FOR PRODUCING THE SAME AND PHARMACEUTICAL COMPOSITIONS CONTAINING THE SAME

TECHNICAL FIELD

The present invention relates to a heparin-binding protein functionalized by covalently bonding thereto heparan sulfate sugar chains selectively, a method for producing the protein, and a pharmaceutical composition containing the protein.

BACKGROUND ART

It has been known that heparin-binding proteins, among all, those proteins classified into the fibroblast growth factor (hereinafter, referred to as "FGF") family strongly bind to heparin and heparan sulfate (sulfated polysaccharides) by a non-covalent bonding mode. It has been also known that when a heparin-binding protein such as fibroblast growth factor is mixed with a sulfated polysaccharide such as heparin, the biological activity and physical properties of the heparin-binding protein are altered to change its function; sometimes, such a heparin-binding protein may acquire higher function. However, even if a sulfated polysaccharide was mixed with, the expected augmentation of the protein function has been limited. Besides, when such a mixture is used as a pharmaceutical composition, undesirable physiological activity attributable to free sulfated polysaccharides has caused some problems.

For the purpose of augmentation of function of heparin-binding proteins, preparation of a heparin-binding protein to which heparan sulfate(s) is(are) selectively conjugated by covalent bond was intended, and a method of producing such a heparin-binding protein was invented. However, according to that invention, the sulfated glycosaminoglycan sugar chains covalently bonded to the heparin-binding protein were a mixture of heparan sulfate and chondroitin sulfate. Since the results of analysis have revealed that augmentation of function of heparin-binding proteins is attributable to heparan sulfate alone, a method of preparing a functionalized heparin-binding protein has been desired by which heparan sulfate is preferentially added and little chondroitin sulfate is added.

Patent document 1: "HEPARIN-BINDING PROTEINS MODIFIED WITH SUGAR CHAINS, METHOD OF PRODUCING THE SAME AND PHARMACEUTICAL COMPOSITIONS CONTAINING SAME", Japanese Patent No. 3318602 (2002), Imamura T, Asada M, Oka S, Suzuki M, Yoneda A, Ota K, Oda Y, Miyakawa K, Orikasa N, Matsuda C, and Kojima T.

Non-patent document 1: Yoneda A, Asada M, Oda Y, Suzuki M, and Imamura T. "Engineering of an FGF-Proteoglycan Fusion Protein with Heparin-Independent, Degradation-Augmented, Mitogenic Activity." Nature Biotechnology 18 (6), 641-644 (2000)

Non-patent document 2: Yoneda A, Asada M, and Imamura T, "Modification of the Activity of Heparin-Binding Growth Factor FGF-1 by Fusion with Syndecan [in Japanese]", Saiboukougaku 19 (9), 1338-1340 (2000)

Non-patent document 3: Asada M, Yoneda A, Imamura T. "Engineering of a Heparin-Binding Growth Factor with Heparan Sulfate Sugar Chains", Trends in Glycoscience and Glycotechnology 13 (72) 385-394 (2001)

DISCLOSURE OF THE INVENTION

Problem for Solution by the Invention

It is an object of the present invention to establish a functionalized heparin-binding protein having glycosaminoglycan sugar chains rich in heparan sulfate but with little chondroitin sulfate covalently bonded thereto and a method of producing the protein, and to provide a pharmaceutical composition containing the protein.

Means to Solve the Problem

As a result of intensive and extensive researches toward the solution of the above-described problem, the present inventors have found that the serine residue at position 39 in the primary structure of natural molecule syndecan-4 (SEQ ID NO: 9) (which is modified with both heparan sulfate and chondroitin sulfate sugar chains at a plurality of sites) is selectively modified with heparan sulfate, by analyzing the sugar chain modification sites of chimeric protein constituted of a part of syndecan-4 and a reporter protein. Focusing on this finding, the inventors have found it possible to produce a heparin-binding protein having intramolecular heparan sulfate sugar chains covalently bonded thereto, by ligating a cDNA (SEQ ID NO: 13) encoding a peptide (SEQ ID NO: 8) which can be modified with heparan sulfate selectively to a cDNA (SEQ ID NO: 10) encoding a heparin-binding protein (SEQ ID NO: 7) and producing the gene product of the resultant ligated cDNA in an animal cell. Further, the inventors have confirmed that the function of this heparan sulfate sugar chain-modified heparin-binding protein is improved. The present invention has been achieved based on these findings.

The present invention provides a heparin-binding protein functionalized by covalently bonding thereto heparan sulfate-rich sugar chains. The functionalized heparin-binding protein of the invention is a heparin-binding protein having at least one sulfated glycosaminoglycan sugar chain covalently bonded thereto, 90% or more of the composition of the sulfated glycosaminoglycan sugar chain being heparan sulfate sugar chain. The composition of sulfated glycosaminoglycan sugar chains may be judged, for example, by the method described in Current Protocols in Molecular Biology, John Wiley & Sons, Inc., UNIT 17.13B (1996).

The sugar chain may be selected from the group consisting of (1) heparan sulfate, (2) N-linked sugar chains combined with heparan sulfate and other glycosaminoglycan, (3) O-linked sugar chains combined with heparan sulfate and other glycosaminoglycan, and (4) a combination thereof. The heparin-binding protein may be a compound belonging to the fibroblast growth factor family or an allied factor thereof. The heparin-binding protein may have heparan sulfate sugar chain (s) covalently bonded thereto through a peptide which can be modified with at least one heparan sulfate sugar chain preferentially. For example, the heparin-binding protein to which sugar chain(s) are to be covalently bonded may be a protein selected from the following (a) or (b):

(a) a protein comprising the amino acid sequence as shown in SEQ ID NO: 6 or 7;
(b) a protein which comprises the amino acid sequence as shown in SEQ ID NO: 6 or 7 but with deletion, substitution, addition or modification of one or several amino acids, which has FGF activity, and which can be modified with at least one heparan sulfate sugar chain preferentially.

The term "FGF activity" specifically refers to activity of promoting or inhibiting the proliferation of fibroblast cells, vascular endothelial cells, myoblast cells, cartilage cells, osteoblast cells and glial cells. FGF activity may be measured according to the method described by Ornitz D M & Leder P., Journal of Biological Chemistry 267 (23), pp. 16305-16311 (1992).

The protein which can be modified with at least one heparan sulfate sugar chain preferentially may be a protein which can be modified with heparan sulfate sugar chain(s) with higher selectivity than other sugar chains (e.g., chondroitin sulfate sugar chains) in an organism having a pathway for heparan sulfate sugar chain biosynthesis. Examples of the organism having a pathway for heparan sulfate sugar chain biosynthesis include, but are not limited to, animal cells (e.g., COS cell, CHO cell, BHK cell, NIH 3T3 cell, BALB/3T3 cell, HUVE cell, LEII cell) and insect cells (e.g., Sf-9 cell, Tn cell).

The present invention also provides a method of producing a heparin-binding protein containing at least one sulfated glycosaminoglycan sugar chain covalently bonded thereto, 90% or more of the composition of the at least one sulfated glycosaminoglycan sugar chain being heparan sulfate sugar chain, wherein the method comprises the following steps:

(a) a step of ligating a cDNA encoding a peptide which can be modified with at least one heparan sulfate sugar chain preferentially to a cDNA encoding a heparin-binding protein;

(b) a step of incorporating the resultant ligated cDNA into an expression vector;

(c) a step of introducing the expression vector into a host cell having a pathway for heparan sulfate sugar chain biosynthesis; and (d) a step of expressing in the host cell a heparin-binding protein to which at least one heparan sulfate sugar chain is covalently bonded through the peptide which can be modified with at least one heparan sulfate sugar chain preferentially.

In the method of the present invention, the peptide which can be modified with at least one sulfate sugar chain preferentially may be a peptide selected from the following (a) or (b):

(a) a peptide comprising the amino acid sequence as shown in SEQ ID NO: 8:

(b) a peptide which comprises the amino acid sequence as shown in SEQ ID NO: 8 but with deletion, substitution, addition or modification of one or several amino acids, and which can be modified with at least one heparan sulfate sugar chain preferentially.

The peptide which can be modified with at least one heparan sulfate sugar chain preferentially may be a peptide which can be modified with heparan sulfate sugar chain(s) with higher selectivity than other sugar chains (e.g., chondroitin sulfate sugar chains) in an organism having a pathway for heparan sulfate sugar chain biosynthesis. Examples of the organism having a pathway for heparan sulfate sugar chain biosynthesis include, but are not limited to, animal cells (e.g., COS cell, CHO cell, BHK cell, NIH 3T3 cell, BALB/3T3 cell, HUVE cell, LEII cell) and insect cells (e.g., Sf-9 cell, Tn cell).

Examples of the cDNA encoding a peptide which can be modified with at least one heparan sulfate sugar chain preferentially include a cDNA having the nucleotide sequence as shown in SEQ ID NO: 13.

In the method of the present invention, the heparin-binding protein is a heparin-binding protein containing at least one sulfated glycosaminoglycan sugar chain covalently bonded thereto, 90% or more of the composition of the at least one sulfated glycosaminoglycan sugar chain being heparan sulfate sugar chain. The sugar chain may be selected from the group consisting of (1) heparan sulfate, (2) N-linked sugar chains combined with heparan sulfate and other glycosaminoglycan, (3) O-linked sugar chains combined with heparan sulfate and other glycosaminoglycan, and (4) a combination thereof. The heparin-binding protein may be a compound belonging to the fibroblast growth factor family or an allied factor thereof. The heparin-binding protein has at least one heparan sulfate sugar chain covalently bonded thereto through a peptide which can be modified with at least one heparan sulfate sugar chain preferentially. For example, the heparin-binding protein to which at least one sugar chain is to be covalently bonded may be a protein selected from the following (a) or (b):

(a) a protein comprising the amino acid sequence as shown in SEQ ID NO: 6 or 7;

(b) a protein which comprises the amino acid sequence as shown in SEQ ID NO: 6 or 7 but with deletion, substitution, addition or modification of one or several amino acids, which has FGF activity, and which can be modified with at least one heparan sulfate sugar chain preferentially.

Further, the present invention provides a pharmaceutical composition containing as an active ingredient the above-described heparin-binding protein functionalized by covalently bonding thereto heparan sulfate sugar chains.

Further, the present invention provides a nucleic acid having the nucleotide sequence as shown in SEQ ID NO: 13 and encoding a peptide which can be modified with at least one heparan sulfate sugar chain preferentially. Examples of nucleic acid include DNA, RNA, chimeric molecules of DNA and RNA, and derivatives thereof. Preferably, the nucleic acid used in the method of preparing the functionalized heparin-binding protein of the invention is DNA.

The term "sulfated glycosaminoglycan sugar chains" used herein is a general term for a wide variety of sugar chain structures which elongate from xylose bound to a serine residue present in the primary structure of proteins or which exist in a free form. They are constructed with a number of disaccharide repeating units containing amino sugar (represented by N-acetylglucosamine and N-acetylgalactosamine) and uronic acid (represented by glucuronic acid and iduronic acid) or galactose, and some of their hydroxyl groups or amino groups are substituted with sulfate groups. Specific structures of sulfated glycosaminoglycan sugar chains are described, for example, in a book titled Destiny of Sugar Chains in Cells (Nagai, Hakomori and Kobata (eds.), Kodansha Scientific). These sulfated glycosaminoglycan sugar chains may have addition, deletion, substitution or modification in a part of their sugar chain sequences as long as they manifest their function.

Effect of the Invention

According to the present invention, a heparin-binding protein containing glycosaminoglycan sugar chains covalently bonding thereto, whose majority was constituted of heparan sulfate but not of chondroitin sulfate, was provided. And a method for preparing such glycoprotein was also provided. The heparin-binding protein of the invention is more highly improved in function than heparin-binding proteins containing heparan sulfate and chondroitin sulfate. The heparin-binding protein of the invention may be used as a pharmaceutical product.

BEST MODE FOR CARRYING OUT THE INVENTION

Figure 1:
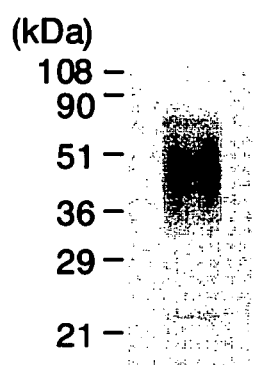
FIG. 1 is an electrophoretic photograph showing the results of staining trunc. PG-FGF-1 protein secreted by COS-1 cells with anti-FGF-1 monoclonal antibody after separation of the protein by SDS denatured electrophoresis in Test Example 1.

Hereinbelow, the present invention will be described in detail.

In the present invention, the heparin-binding protein to which heparan sulfate sugar chains are to be covalently bonded is a protein having heparin binding property. For example, factors belonging to the FGF family or allied factors, or other proteins with heparin-binding property but without structural similarity to the former proteins may be enumerated. Examples of the other proteins include, but are not limited to, heparin-binding epidermal growth factor-like factor (HB-EGF) and platelet-derived growth factor (PDGF). As specific examples of the factors belonging to the FGF family, FGF-1 to -23 are known. The heparin-binding protein of the invention may be covalently bonded to heparan sulfate sugar chains through a peptide which can be modified with sugar chains. For example, the heparin-binding protein to which heparan sulfate sugar chains are to be covalently bonded may be a protein selected from the following (a) or (b):

(a) a protein containing the amino acid sequence of SEQ ID NO: 7;
(b) a protein which contains the amino acid sequence of SEQ ID NO: 7 but with deletion, substitution, addition or modification of one or several amino acids, which has FGF activity and which can be modified with at least one heparan sulfate sugar chain preferentially.

A protein having the amino acid sequence as shown in SEQ ID NO: 7 is encoded, for example, by the DNA sequence as shown in SEQ ID NO: 10. Alternatively, the heparin-binding protein to which heparan sulfate sugar chains are to be covalently bonded may be a protein selected from the following (a') or (b'):

(a') a protein containing the amino acid sequence of SEQ ID NO: 6;
(b') a protein which contains the amino acid sequence of SEQ ID NO: 6 but with deletion, substitution, addition or modification of one or several amino acids, which has FGF activity and which can be modified with at least one heparan sulfate sugar chain preferentially.

A protein having the amino acid sequence as shown in SEQ ID NO: 6 is encoded, for example, by the DNA sequence as shown in SEQ ID NO: 5. This protein comprises a peptide sequence which can be modified with at least one heparan sulfate sugar chain preferentially and a signal peptide sequence, in addition to the peptide sequence for a protein belonging to the FGF family. The term "heparin-binding protein" used herein includes not only the protein primarily defined by a cDNA shown in the Sequence Listing but also a protein in which a peptide sequence for secretion, called as signal peptide, located at the amino terminus has been truncated when secreted from cells. The utility of a heparin-binding protein which is contained in the pharmaceutical composition of the invention as an active ingredient will not vary even when the protein is produced in a truncated form lacking the signal peptide from the beginning.

The heparan sulfate sugar chain(s) to be covalently bonded to the heparin-binding protein may be any heparan sulfate sugar chain(s) as long as the protein is functionalized by covalently bonding thereto the sugar chain(s). The term "functionalize" used herein means increasing the activity of a protein of interest. As an example of functionalization, there may be given a case in which the residual activity of a protein after treatment with heat, acid or alkali is increased by covalently bonding heparan sulfate sugar chain(s) thereto. The "heparan sulfate sugar chain(s)" used herein is the above-described sulfated glycosaminoglycan sugar chain(s) which are constructed with a number of disaccharide repeating units containing N-acetylglucosamine (as amino sugar) and glucuronic acid or iduronic acid (as uronic acid) and in which some of their hydroxyl groups or amino groups are substituted with sulfate groups. These heparan sulfate sugar chains may have addition, deletion, substitution or modification in a part of their sugar chain sequences as long as they manifest their function.

When heparan sulfate sugar chain(s) are conjugated to a heparin-binding protein, the sugar chain(s) alone may be covalently bonded to the heparin-binding protein directly. Alternatively, a peptide chain of any length to which sugar chain(s) are covalently bonding may be covalently bonded to a heparin-binding protein. In order to prepare the heparin-binding protein of the invention to which heparan sulfate sugar chain(s) are covalently bonded (hereinafter, referred to as the "heparan sulfate-modified heparin-binding protein"), first, a cDNA encoding a peptide which can be modified with heparan sulfate sugar chain(s) preferentially is ligated to a cDNA encoding a heparin-binding protein. The ligated cDNA is incorporated into an appropriate expression vector, which is then introduced into a host cell having sugar chain biosynthetic pathway(s) to thereby express a heparan sulfate-modified heparin-binding protein of interest.

cDNAs encoding various heparin-binding proteins can be obtained by designing appropriate primers from sequences registered in gene banks such as DDBJ (DNA Data Bank of Japan) and performing RT-PCR (reverse transcription-PCR) with the primers and mRNA from a relevant tissue of a relevant animal.

As a peptide which is known to be modified with at least one heparan sulfate sugar chain preferentially, the core protein or a part thereof of various proteoglycans (e.g. syndecan, glypican and perlecan) may be used. As a part of the core protein of a proteoglycan, a peptide containing a Ser-Gly repeat sequence (which is believed to be the sugar chain attachment site in proteoglycans) may be used. Examples of the peptide which can be modified with at least one heparan sulfate sugar chain preferentially include a peptide selected from the following (a) or (b):

(a) a peptide containing the amino acid sequence as shown in SEQ ID NO: 8:
(b) a peptide which contains the amino acid sequence as shown in SEQ ID NO: 8 but with deletion, substitution, addition or modification of one or several amino acids, and which can be modified with at least one heparan sulfate sugar chain preferentially.

As the site to which heparan sulfate sugar chain(s) are bonded, a site forming a turn in the secondary structure of a heparin-binding protein or a site near one of the ends, or a site which would not change the tertiary structure of the protein greatly by modification with the sugar chain(s) is preferred.

One example of the method for producing a heparan sulfate sugar chain-modified heparin-binding protein of the invention will be described below.

First, an oligonucleotide encoding a secretion signal peptide and a peptide which is known to be modified with at least one heparan sulfate sugar chain preferentially is synthesized or amplified by PCR. The resultant oligonucleotide is incorporated at the 5' end of a plasmid encoding a heparin-binding protein. As the secretion signal peptide, a part of the amino terminal region of a typical secretion-type glycoprotein may be used, for example. Specifically, the peptide consisting of the N terminal 18 amino acid residues of human syndecan-4 may be used. The plasmid encoding a heparin-binding protein may be prepared by incorporating a DNA encoding the heparin-binding protein into an appropriate plasmid. As the plasmid into which a DNA encoding a heparin-binding protein is to be incorporated, any plasmid may be used as long as it is replicated and maintained in a host. For example, pBR322 and pUC18 from $E.$ $coli$ and pET-3c which was constructed based on these plasmids may be enumerated. As a method for incorporating the above-described oligonucleotide into the plasmid encoding a heparin-binding protein, the method described in T. Maniatis et al.: Molecular Cloning, Cold Spring Harbor Laboratory, p. 239 (1982) may be given, for example.

From the thus prepared plasmid, a region containing a nucleotide sequence encoding a secretion signal peptide, a peptide which is known to be modified with heparan sulfate sugar chain(s) preferentially and a heparin-binding protein (hereinafter, referred to as a "region containing a nucleotide sequence encoding a heparan sulfate sugar chain-modified heparin-binding protein") is extracted. This region is ligated downstream of a promoter in a vector suitable for expression to thereby obtain a protein-expressing vector. The above-described region containing a nucleotide sequence encoding a heparan sulfate sugar chain-modified heparin-binding protein may have ATG at its 5' end as a translation initiation codon and TAA, TGA or TAG at its 3' end as a translation termination codon. In order to allow expression of the protein encoded in the coding region, a promoter is ligated upstream of this region. As the promoter to be used in the present invention, any promoter may be used as long as it is appropriate to the host used for the expression of the gene. When the host to be transformed is an animal cell, a promoter from SV40 or a promoter from a retrovirus may be used. As the plasmid into which the thus constructed recombinant DNA having a nucleotide sequence encoding a heparan sulfate sugar chain-modified heparin-binding protein is to be incorporated, any plasmid may be used as long as it can be expressed in the host cell. For example, those vectors which were constructed based on $E.$ $coli$-derived pBR322 and pUC18 may be given. As a method for incorporating the recombinant DNA into a plasmid, the method described in T. Maniatis et al.: Molecular Cloning, Cold Spring Harbor Laboratory, p. 239 (1982) may be given, for example.

By introducing a vector containing the above-described recombinant DNA into a host cell, a transformant carrying the vector is prepared. As the host cell, any cell may be used as long as it has pathways for heparan sulfate sugar chain biosynthesis. Specific examples include, but are not limited to, animal cells (e.g. COS cell, CHO cell, BHK cell, NIH3T3 cell, BALB/3T3 cell, HUVE cell, LEII cell) and insect cells (e.g. Sf-9 cell, Tn cell).

The above-mentioned transformation may be performed by a conventional method commonly used for each host. Alternatively, an applicable method may be used though it is not commonly used. For example, when the host is an animal cell, a vector containing the recombinant DNA is introduced into cells at the logarithmic growth phase or the like by the calcium phosphate method, lipofection or electroporation.

By culturing the thus obtained transformant in a medium, a heparan sulfate sugar chain-modified heparin-binding protein is produced. As the medium for culturing the transformant, a conventional medium commonly used for each host may be used. Alternatively, an applicable medium may be used even if it is not commonly used. For example, when the host is an animal cell, Dulbecco's MEM supplemented with animal serum, or the like may be used. The cultivation may be performed under conditions commonly employed for each host. Alternatively, applicable conditions may be used even if they are not commonly used. For example, when the host is an animal cell, the cultivation is carried out at about 32 to 37° C. under 5% $CO_2$ and 100% humidity for about 24 hours to 2 weeks. If necessary, the conditions of the gas phase may be changed or agitation may be carried out.

In order to obtain the heparan sulfate sugar chain-modified heparin-binding protein from the culture of the above-described transformant, the protein secreted into the conditioned medium may be directly collected from a supernatant after centrifugation. In order to purify the heparan sulfate sugar chain-modified heparin-binding protein from the above-mentioned supernatant, known separation/purification methods may be used in an appropriate combination. Specific examples of these known separation/purification methods include salting out, solvent precipitation, dialysis, ultrafiltration, gel filtration, SDS-polyacrylamide gel electrophoresis, ion exchange chromatography, affinity chromatography, reversed phase high performance liquid chromatography, isoelectric focusing and so on. The thus obtained sample may be dialyzed and lyophilized to obtain dry powder as long as the activity of the heparan sulfate sugar chain-modified heparin-binding protein is not damaged by such processing. Further, in storing the sample, addition of serum albumin as a carrier to the sample is effective for preventing adsorption of the sample to the container. The inclusion of an extremely small amount of a reducing agent in the purification process or the storing process is preferable for preventing oxidation of the sample. As the reducing agent, β-mercaptoethanol, dithiothreitol, glutathione or the like may be used.

The heparan sulfate sugar chain-modified heparin-binding protein of the invention may also be produced by conjugating sugar chain(s) to a heparin-binding protein by a chemical method. As the specific method, the following a) or b), or a combination thereof may be used.

a) For example, first, heparan sulfate sugar chain(s) are completed by a biological method, a chemical synthesis method or a combination thereof. At that time, a residue appropriate for protein binding may be introduced at one end of the sugar chain(s). For example, an aldehyde group is formed by reducing and partially oxidizing the reducing end of the completed sugar chain. Then, this aldehyde group is conjugated to an amino group in a protein by an amino bond to thereby complete the joining of the sugar chain and the protein.

b) For example, first, an aldehyde group is formed by reducing and partially oxidizing the reducing end of a monosaccharide or a residue appropriate for protein binding which is bound to a monosaccharide. Then, this aldehyde group is conjugated to an amino group in a protein by an amino bond to thereby complete the joining of the monosaccharide and the protein. Additional monosaccharide(s), sugar chain(s) or the like are conjugated to functional groups such as hydroxyl group of the above monosaccharide to thereby complete heparan sulfate sugar chains. For this conjugation, a biological method, a chemical synthesis method or a combination thereof may be considered.

A heparin-binding protein functionalized by covalently bonding thereto heparan sulfate sugar chain(s) can be used as a medicine. For example, the heparan sulfate sugar chain-modified heparin-binding protein of the invention regulates the physiological function of FGF. Specifically, the physiological function of FGF is to promote or inhibit the growth of fibroblast cells, vascular endothelial cells, myoblast cells, cartilage cells, osteoblast cells and glia cells. Therefore, the heparan sulfate sugar chain-modified heparin-binding protein of the invention is effective for promoting cell growth and tissue regeneration in liver or the like; for curing wounds and regulating nervous function; and for regulating the growth of fibroblast cells or the like. The protein of the invention is useful for preventing or treating various diseases such as fibroblastoma, angioma, osteoblastoma, death of neurocytes, Alzheimer's disease, Parkinson's disease, neuroblastoma, amnesia, demensia and myocardial infarction. The protein of the invention may also be used as a trichogenous agent or a hair-growing agent.

The heparan sulfate sugar chain-modified heparin-binding protein of the invention may be formulated into pharmaceutical compositions such as liquid, lotions, aerosols, injections, powder, granules, tablets, suppositories, enteric coated tablets and capsules, by mixing the protein with pharmaceutically acceptable solvents, vehicles, carriers, adjuvants, etc. according to conventional formulation methods. The content of the heparan sulfate sugar chain-modified heparin-binding protein, which is an active ingredient, in the pharmaceutical composition may be about 0.0000000001 to 1.0% by weight. The pharmaceutical composition can be administered parenterally or orally to mammals, e.g. human, mouse, rat, rabbit, dog, cat, etc. in a safe manner. The dose of the pharmaceutical composition may be appropriately changed depending on the dosage form, administration route, conditions of the patient and the like. For example, for administration to mammals including human, 0.0001 to 100 mg of the heparan sulfate sugar chain-modified heparin-binding protein may be applied to the diseased site several times a day.

The present invention has been described so far taking heparin-binding proteins as an example. However, it should be noted that besides the heparin-binding proteins, natural proteins having no sugar chains can also be functionalized by covalently conjugating thereto sugar chains.

Deposit of Microorganisms

An *E. coli* DH5α clone carrying a plasmid incorporating a gene encoding a heparan sulfate sugar chain-modified heparin-binding protein of the invention (having the DNA sequence as shown in SEQ ID NO: 11) was deposited at the International Patent Organism Depository, National Institute of Advanced Industrial Science and Technology under Accession Number FERM P-16412 on Sep. 10, 1997.

EXAMPLES

Hereinbelow, the present invention will be described specifically with reference to the following Examples. However, the present invention is not limited to these Examples.

Reference Example 1

Construction of S/FGF-1a-II/pMEXneo Plasmid

1) Construction of S/FGF-1a-II Plasmid

1. Preparation of a Human Ryudocan cDNA Fragment phR7A8 is a plasmid obtained by inserting a human ryudocan cDNA (PCR product) into the EcoR V site of pBluescript II (KS+) cloning vector. This plasmid contains a partial sequence from position 7 to position 2610 of the mRNA sequence as shown under Accession No. D13292 (see B.B.R.C. Vol. 190, No. 3, pp. 814-822, 1993). This plasmid was digested with Pvu II. Using the resultant DNA fragment of 2,232 base pairs as a template, a PCR (polymerase chain reaction) was performed. As primers, #109 (5'-TTG TCG ACC CAC CAT GGC CCC CGC CCG TCT-3') (SEQ ID NO: 15) and #111 (5'-TTG ATA TCT AGA GGC ACC AAG GGA TG-3') (SEQ ID NO: 16) were used. The specifically amplified 276 bp band was separated by electrophoresis, extracted and double-digested with EcoR V and Sal I. The resultant 268 bp band was separated, extracted and then used in the ligation described below.

2. Preparation of FGF-1a/pBluescript II (KS+)

A PCR was performed using human FGF-1 cDNA as a template and #967 (5'-GCG TCG ACA GCG CTA ATT ACA AGA AGC CCA AAC TC-3') (SEQ ID NO: 17) and #630 (5'-CCG AAT TCG AAT TCT TTA ATC AGA AGA GAC TGG-3') (SEQ ID NO: 18) as primers. The specifically amplified 434 bp band was separated by electrophoresis, extracted and double-digested with EcoR I and Sal I. The resultant 422 bp band was separated, extracted and then inserted into pBluescript II (KS+) cloning vector (2934 bp) double-digested with EcoR I and Sal I, to thereby prepare FGF-1a/pBluescript 1a/pBluescript II (KS+). This FGF-1a/pBluescript II (KS+) was digested with Aor51H I and Sal I in this order. The resultant 2626 bp band was separated, extracted and then used in the ligation described below.

3. Preparation of S/FGF-1a-II Chimeric Gene

EcoR V/Sal I fragment from the human ryudocan PCR product and Aor51 H I/Sal I fragment from FGF-1a/pBluescript II (KS+) were subjected to a DNA ligation to produce S/FGF-1a-II/pBluescript II (KS+) vector. Subsequently, this vector was double-digested with EcoR I and Sal I to give a 678 bp band, which was then separated and extracted. The resultant fragment was inserted into pMEXneo expression vector (5916 bp) double-digested with EcoR I and Sal I, to thereby prepare S/FGF-1a-II/pMEXneo. This protein-expressing vector contains the nucleotide sequence as shown in SEQ ID NO: 11.

Example 1

Preparation of trunc. PG-FGF-1 Protein

1. Construction of Trunc. PG-FGF-1 Plasmid (1) Construction of a Gene for the Former Part of Trunc. PG-FGF-1

Using S/FGF-1a-II/pMEXneo plasmid (Reference Example 1) as a template, a PCR (polymerase chain reaction) was performed. As primers, #117 (5'-tcttccgatagactgcgtcg-3') (SEQ ID NO: 1) and #645 (5'-gtaattagctacatcctcatcgtctgg-3') (SEQ ID NO: 2) were used. A specifically amplified 200 bp band was separated by electrophoresis and extracted.

The DNA sequence of the coding region carried by S/FGF-1a-II/pMEXneo plasmid is shown in SEQ ID NO: 11. This sequence encodes a protein having the amino acid sequence as shown in SEQ ID NO: 12 in mammal cells.

(2) Construction of a Gene for the Latter Part of Trunc. PG-FGF-1

Using S/FGF-1a-II/pMEXneo plasmid as a template, a PCR was performed. As primers, #646 (5'-gaggatgtagctaat-tacaagaagccca-3') (SEQ ID NO: 3) and #118 (5'-cattctagttgtg-gtttgtcc-3') (SEQ ID NO: 4) were used. A specifically amplified 479 bp band was separated by electrophoresis and extracted.

(3) Construction of a Full-Length Gene for Trunc. PG-FGF-1

Using the DNA fragments obtained in (1) and (2) above in mixture as a template, a PCR was performed. As primers, #117 and #118 were used. A specifically amplified 661 bp band was separated by electrophoresis and extracted. The resultant DNA was double-digested with EcoR I and Sal I. The resultant 564 bp band was separated and extracted. This fragment was inserted into pMEXneo expression vector (5916 base pairs) double-digested with EcoR I and Sal I to thereby obtain trunc. PG-FGF-1/pMEXneo. This expression vector contains the nucleotide sequence as shown in SEQ ID NO: 5, which encodes a protein having the amino acid sequence as shown in SEQ ID NO: 6 in mammal cells.

2. Expression of Trunc. PG-FGF-1 Protein

The resultant trunc. PG-FGF-1/pMEXneo was introduced into COS-1 cells (simian kidney-derived cell line) by lipofection. The cells were cultured in a serum-free medium to thereby allow secretion of the biosynthesized protein into the medium. Three days after the start of the cultivation, the culture supernatant was collected. The resultant conditioned medium was subjected to low speed centrifigation, and the supernatant was stored at 4° C.

3. Crude Purification of Trunc. PG-FGF-1 Protein by Anion Exchange Chromatography DEAE (diethylaminoethyl)-Sepharose beads were added to the conditioned medium of trunc. PG-FGF-1 protein-secreting cells and agitated at 4° C. Beads precipitated by low speed centrifugation were collected and packed in a column. The beads were washed with 0.001% CHAPS (cholamidopropyl-dimethylammonio-propanesulfonate)-containing Tris-HCl buffer (10 mM, pH 7.4) thoroughly. Then, the protein bound thereto was eluted with the same buffer containing 0.5 M NaCl. Further, the eluate was dialyzed against phosphate buffered saline (PBS, pH 7.4).

Test Example 1

SDS Denatured Electrophoresis

The conditioned medium of trunc. PG-FGF-1 protein-secreting cells was dialyzed against distilled water and then concentrated by lyophilization. The concentrated medium was boiled with sample buffer (containing SDS and 2-mercaptoethanol) to prepare a sample for electrophoresis. Using 12.5% poly-acrylamide gel, electrophoresis was performed in the presence of SDS and 2-mercaptoethanol. The separated proteins were electrically transferred onto a nitrocellulose membrane and stained with anti-FGF-1 monoclonal antibody and horse radish peroxidase-linked anti-mouse IgG antibody, followed by detection by chemiluminescence. The results are shown in FIG. 1. In this figure, the running positions and individual molecular weights (kDa) of standard proteins having known molecular weights are shown on the left side.

Trunc. PG-FGF-1 protein is a protein having the 183 amino acid residues as shown in SEQ ID NO: 6. When this protein is expressed and secreted as a simple protein without modification, a band should appear at approx. 20 kDa. Actually, however, a smear band was detected at around 40 kDa to 100 kDa. This is a pattern characteristic for proteins modified with glycosaminoglycan sugar chains. It is believed that the band became smear because the glycosaminoglycan sugar chains had various lengths.

Test Example 2

Treatment with Carbohydrate Degrading Enzymes

Figure 2:
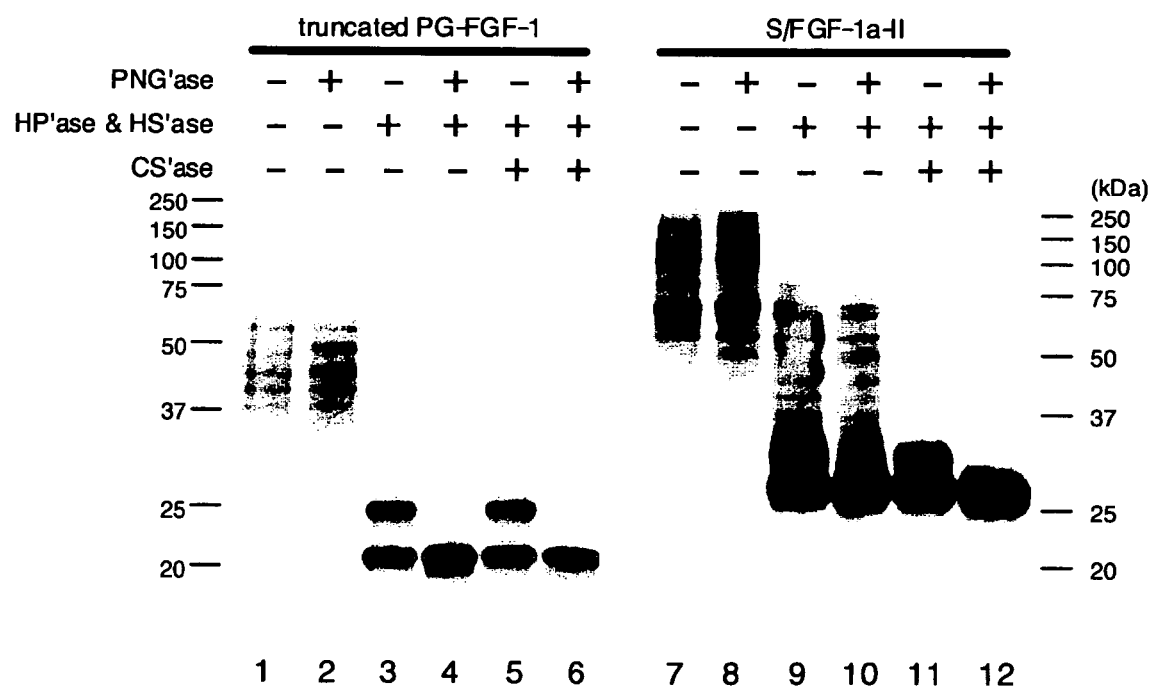
FIG. 2 is electrophoretic photographs showing the results of analysis by staining trunc. PG-FGF-1 protein and S/FGF-1a-II protein with anti-FGF-1 monoclonal antibody after these proteins were treated with various glycosaminoglycan degrading enzymes (GAG'ases) and peptide N-glycosidase F and then subjected to SDS denatured electrophoresis in Test Example 2.

The trunc. PG-FGF-1 protein concentrated by lyophilization as described in Test Example 1 was treated with various glycosaminoglycan degrading enzymes (GAG'ases) and then with peptide N-glycosidase F. The thus treated protein was analyzed by SDS denatured electrophoresis in the same manner as in Test Example 1. For comparison, S/FGF-1a-II/pMEXneo prepared in Reference Example 1 was also analyzed in the same manner. The results are shown in FIG. 2. The left panel shows the results on trunc. PG-FGF-1 protein, and the right panel shows the results on S/FGF-1a-II. The running positions of molecular markers are shown on both sides. Trunc. PG-FGF-1 gives two definite bands at 21 kDa and 25 kDa and treatment with a mixture of heparanase and haparitinase (HP'ase & HS'ase) eliminates all smear bands (lane 3). On the other hand, in case of S/FGF-1a-II, treatment with a mixture of heparanase and haparitinase (HP'ase & HS'ase) alone cannot eliminate smear bands completely, though a part of this protein shifted to represent a sharp band at 25 kDa (lane 9). Smear bands disappear only when chondroitinase (CS'ase) is further added thereto (lane 11). These results revealed that, while S/FGF-1a-II is modified not only with heparan sulfate but also with chondroitin sulfate, trunc. PG-FGF-1 is modified with heparan sulfate alone. Further, for the purpose of analyzing the two bands appearing after the treatment with HP'ase & HS'ase and CS'ase (lane 3 and lane 11), peptide N-glycosidase F (an enzyme which liberates every N-linked sugar chain) was added. As a result, the band located on the high molecular weight side disappeared to leave one band (lane 4 and lane 12). These results revealed that both trunc. PG-FGF-1 and S/FGF-1a-II are also modified with N-linked sugar chains, though partially.

Test Example 3

Cell Proliferation Promoting Activity

The physiological activity of trunc. PG-FGF-1 protein as a growth factor was evaluated. When FGF-1 binds to its receptor in a target cell and exhibits its physiological activity, co-existence of heparin or heparan sulfate is essential. Then, the cell proliferation promoting activity of trunc. PG-FGF-1 protein was evaluated in the presence or absence of exogenous heparin, using mouse pro B cell-derived Ba/F3 cells, which are known to express no endogenous heparan sulfate, expressing an FGF receptor (R1c type) as a target cell. The evaluation was performed based on viable cell count using TetraColor ONE.

Figure 3:
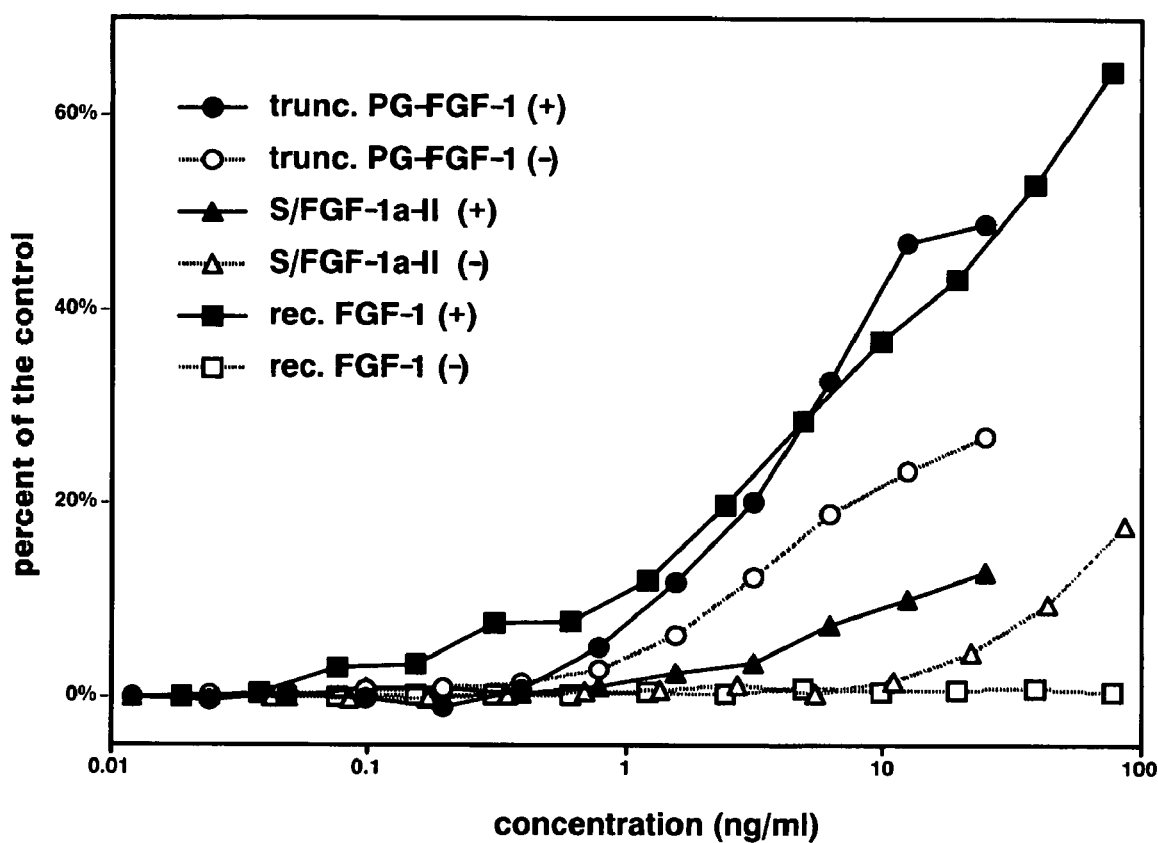
FIG. 3 is a graph showing the results of evaluation of the cell proliferation promoting activity of various proteins on Ba/F3 cells expressing FGF receptors.

FGF-receptor expressing Ba/F3 cells were plated in 96-well plates. Simultaneously, semi-purified trunc. PG-FGF-1 protein was added thereto at various concentrations. At this time, samples with or without 10 μg of heparin were prepared. After 48 hours, TetraColor ONE (10 μl) was added and incubated for another 4 hours. Then, absorbance at 450 nm was measured. For comparison, S/FGF-1a-II/pMEX-neo prepared in Reference Example 1 and a simple protein FGF-1 produced by *E. coli* were also analyzed in the same manner. The results are shown in FIG. 3.

In this figure, circles represent the cell proliferation promoting activity of trunc. PG-FGF-1 protein; triangles represent the cell proliferation promoting activity of S/FGF-1a-II protein; and squares represent the cell proliferation promoting activity of the simple protein FGF-1 produced by *E. coli*. Solid lines represent the case in the presence of heparin (5 μg/ml) and dotted lines represent the case in the absence of heparin. Cell proliferation promoting activities in the presence of various growth factors are measured as absorbance at 450 nm and given in % taking the absorbance at 450 nm of Ba/F3 cells cultured in a growth medium (containing IL-3) as 100%.

In the simple protein FGF-1 produced by *E. coli*, a concentration-dependent cell proliferation promoting activity was only detected in the presence of heparin (square, solid line). However, no activity was detected in the absence of heparin (square, dotted line).

In S/FGF-1a-II protein, some activity was observed at high concentrations (10-100 ng/ml) even in the absence of heparin (triangle, dotted line). Trunc. PG-FGF-1 protein manifested activity even at low concentrations (1-10 ng/ml) in the absence of heparin (circle, dotted line). This activity is equivalent to the activity of simple protein FGF-1 in the presence of heparin (square, solid line); and trunc. PG-FGF-1 protein has higher specific activity than S/FGF-1a-II protein. From these results, it is believed that since S/FGF-1a-II protein and trunc. PG-FGF-1 protein have heparan sulfate sugar chains within their molecules (see FIG. 2), these heparan sulfate sugar chains substitute for the function of heparin. However, not only heparan sulfate sugar chains but also chondroitin sulfate sugar chains which are believed not to contribute to the manifestation of activity are attached to S/FGF-1a-II protein, and thus the specific activity of this protein is not so high. On the other hand, it is believed that since trunc. PG-FGF-1 protein is modified with almost heparan sulfate sugar chains alone, the protein exhibited a high specific activity. These results have shown that it is more effective to design molecules modified with heparan sulfate alone than with a mixture of heparan sulfate and chondroitin sulfate in the remodeling of physiologically active factors which require co-existence of heparin or heparan sulfate for manifestation of their activity into factors which can manifest activity even in the absence of sugar chains.

INDUSTRIAL APPLICABILITY

The novel, heparan sulfate sugar chain-modified heparin-binding protein of the present invention is excellent in stabilities, such as thermostability, acid resistance, alkali resistance and resistance to proteolytic enzymes, and has high biological activity. Therefore, by using the heparan sulfate sugar chain-modified heparin-binding protein of the invention in pharmaceutical products, it is possible to design such a pharmaceutical product that is excellent in in vivo stabilities, that makes it possible for oral application and that is highly effective.

Sequence Listing Free Text

<SEQ ID NO: 1>
SEQ ID NO: 1 shows the nucleotide sequence of primer #117 used in Example 1.

<SEQ ID NO: 2>
SEQ ID NO: 2 shows the nucleotide sequence of primer #645 used in Example 1.

<SEQ ID NO: 3>
SEQ ID NO: 3 shows the nucleotide sequence of primer #646 used in Example 1.

<SEQ ID NO: 4>
SEQ ID NO: 4 shows the nucleotide sequence of primer #118 used in Example 1.

<SEQ ID NO: 5>
SEQ ID NO: 5 shows the nucleotide sequence of trunc. PG-FGF-1.

<SEQ ID NO: 6>
SEQ ID NO: 6 shows the amino acid sequence of trunc. PG-FGF-1.

<SEQ ID NO: 7>
SEQ ID NO: 7 shows the amino acid sequence of FGF-1a.

<SEQ ID NO: 8>
SEQ ID NO: 8 shows a partial amino acid sequence of human syndecan-4.

<SEQ ID NO: 9>
SEQ ID NO: 9 shows the entire amino acid sequence of human syndecan-4.

<SEQ ID NO: 10>
SEQ ID NO: 10 shows the nucleotide sequence of FGF-1a.

<SEQ ID NO: 11>
SEQ ID NO: 11 shows the nucleotide sequence of S/FGF-1a-II.

<SEQ ID NO: 12>
SEQ ID NO: 12 shows the amino acid sequence of S/FGF-1a-II.

<SEQ ID NO: 13>
SEQ ID NO: 13 shows a partial nucleotide sequence of human syndecan-4.

<SEQ ID NO: 14>
SEQ ID NO: 14 shows the entire nucleotide sequence of human syndecan-4.

<SEQ ID NO: 15>
SEQ ID NO: 15 shows the nucleotide sequence of primer #109 used in Reference Example 1.

<SEQ ID NO: 16>
SEQ ID NO: 16 shows the nucleotide sequence of primer #111 used in Reference Example 1.

<SEQ ID NO: 17>
SEQ ID NO: 17 shows the nucleotide sequence of primer #967 used in Reference Example 1.

<SEQ ID NO: 18>
SEQ ID NO: 18 shows the nucleotide sequence of primer #630 used in Reference Example 1.

The invention claimed is:

1. A method of producing a heparin-binding protein having at least one sulfated glycosaminoglycan sugar chain covalently bonded thereto, wherein 90% or more of said at least one sulfated glycosaminoglycan sugar chain being a heparan sulfate sugar chain, wherein the method comprises:
   (a) a step of ligating a cDNA encoding a peptide consisting of an amino acid sequence shown in SEQ ID NO: 8 which is capable of being modified with at least one heparan sulfate sugar chain to a cDNA encoding a heparin-binding protein;
   (b) a step of incorporating the resultant ligated cDNA into an expression vector;
   (c) a step of introducing the expression vector into a host cell having a pathway for heparan sulfate sugar chain biosynthesis; and
   (d) a step of expressing in the host cell a heparin-binding protein to which at least one heparan sulfate sugar chain is covalently bonded through the peptide consisting of the amino acid sequence shown in SEQ ID NO: 8.

2. The method of claim 1, wherein the cDNA encoding the peptide consists of a nucleotide sequence as shown in SEQ ID NO: 13.

3. The method of claim 1, wherein the heparin-binding protein is a compound belonging to the fibroblast growth factor family.

4. A nucleic acid consisting of the nucleotide sequence as shown in SEQ ID NO: 13 and encoding a peptide which is capable of being modified with at least one heparan sulfate sugar chain.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: synthetic DNA

<400> SEQUENCE: 1
tcttccgata gactgcgtcg                                                     20

<210> SEQ ID NO 2
<211> LENGTH: 27
<212> TYPE: DNA
<213> ORGANISM: Artificial
<220> FEATURE:
<223> OTHER INFORMATION: synthetic DNA

<400> SEQUENCE: 2
gtaattagct acatcctcat cgtctgg                                             27

<210> SEQ ID NO 3
<211> LENGTH: 28
<212> TYPE: DNA
<213> ORGANISM: Artificial
<220> FEATURE:
<223> OTHER INFORMATION: synthetic DNA

<400> SEQUENCE: 3
gaggatgtag ctaattacaa gaagccca                                            28

<210> SEQ ID NO 4
<211> LENGTH: 21
<212> TYPE: DNA
<213> ORGANISM: Artificial
<220> FEATURE:
<223> OTHER INFORMATION: synthetic DNA

<400> SEQUENCE: 4
cattctagtt gtggtttgtc c                                                   21

<210> SEQ ID NO 5
<211> LENGTH: 549
<212> TYPE: DNA
<213> ORGANISM: Artificial
<220> FEATURE:
<223> OTHER INFORMATION: synthetic DNA

<400> SEQUENCE: 5
atggcccccg cccgtctgtt cgcgctgctg ctgttcttcg taggcggagt cgccgagtcg         60
atccgagaga ctgaggtcat cgaccccag gacctcctag aaggccgata cttctccgga        120
gccctaccag acgatgagga tgtagctaat tacaagaagc ccaaactcct ctactgtagc        180
aacgggggcc acttcctgag gatccttccg gatggcacag tggatgggac aagggacagg        240
agcgaccagc acattcagct gcagctcagt gcggaaagcg tgggggaggt gtatataaag        300
agtaccgaga ctggccagta cttggccatg acaccgacg gcttttata cggctcacag         360 acaccaaatg aggaatgttt gttcctggaa aggctggagg agaaccatta caacacctat        420
atatccaaga agcatgcaga gaagaattgg tttgttggcc tcaagaagaa tgggagctgc        480
aaacgcggtc ctcggactca ctatggccag aaagcaatct tgtttctccc cctgccagtc        540
tcttctgat                                                                 549

<210> SEQ ID NO 6
<211> LENGTH: 183
<212> TYPE: PRT
<213> ORGANISM: Artificial
<220> FEATURE:
<223> OTHER INFORMATION: chimeric molecule

<400> SEQUENCE: 6

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Ala Asn Tyr Lys Lys Pro Lys Leu Leu Tyr Cys Ser Asn Gly Gly His
    50                  55                  60

Phe Leu Arg Ile Leu Pro Asp Gly Thr Val Asp Gly Thr Arg Asp Arg
65                  70                  75                  80

Ser Asp Gln His Ile Gln Leu Gln Leu Ser Ala Glu Ser Val Gly Glu
                85                  90                  95

Val Tyr Ile Lys Ser Thr Glu Thr Gly Gln Tyr Leu Ala Met Asp Thr
            100                 105                 110

Asp Gly Leu Leu Tyr Gly Ser Gln Thr Pro Asn Glu Glu Cys Leu Phe
        115                 120                 125

Leu Glu Arg Leu Glu Glu Asn His Tyr Asn Thr Tyr Ile Ser Lys Lys
    130                 135                 140

His Ala Glu Lys Asn Trp Phe Val Gly Leu Lys Lys Asn Gly Ser Cys
145                 150                 155                 160

Lys Arg Gly Pro Arg Thr His Tyr Gly Gln Lys Ala Ile Leu Phe Leu
                165                 170                 175

Pro Leu Pro Val Ser Ser Asp
            180

<210> SEQ ID NO 7
<211> LENGTH: 136
<212> TYPE: PRT
<213> ORGANISM: Homo sapiens

<400> SEQUENCE: 7

Met Ala Asn Tyr Lys Lys Pro Lys Leu Leu Tyr Cys Ser Asn Gly Gly
1               5                   10                  15

His Phe Leu Arg Ile Leu Pro Asp Gly Thr Val Asp Gly Thr Arg Asp
            20                  25                  30

Arg Ser Asp Gln His Ile Gln Leu Gln Leu Ser Ala Glu Ser Val Gly
        35                  40                  45

Glu Val Tyr Ile Lys Ser Thr Glu Thr Gly Gln Tyr Leu Ala Met Asp
    50                  55                  60

Thr Asp Gly Leu Leu Tyr Gly Ser Gln Thr Pro Asn Glu Glu Cys Leu
65                  70                  75                  80

Phe Leu Glu Arg Leu Glu Glu Asn His Tyr Asn Thr Tyr Ile Ser Lys
                85                  90                  95

Lys His Ala Glu Lys Asn Trp Phe Val Gly Leu Lys Lys Asn Gly Ser
            100                 105                 110

Cys Lys Arg Gly Pro Arg Thr His Tyr Gly Gln Lys Ala Ile Leu Phe

```
                115                 120                 125
Leu Pro Leu Pro Val Ser Ser Asp
    130                 135

<210> SEQ ID NO 8
<211> LENGTH: 48
<212> TYPE: PRT
<213> ORGANISM: Homo sapiens

<400> SEQUENCE: 8

Met Ala Pro Ala Arg Leu Phe Ala Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

<210> SEQ ID NO 9
<211> LENGTH: 198
<212> TYPE: PRT
<213> ORGANISM: Homo sapiens

<400> SEQUENCE: 9

Met Ala Pro Ala Arg Leu Phe Ala Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Leu Ala Ala Leu Ile Val Gly Gly Ile Val Gly Ile Leu Phe
145                 150                 155                 160

Ala Val Phe Leu Ile Leu Leu Leu Met Tyr Arg Met Lys Lys Lys Asp
                165                 170                 175

Glu Gly Ser Tyr Asp Leu Gly Lys Lys Pro Ile Tyr Lys Lys Ala Pro
            180                 185                 190

Thr Asn Glu Phe Tyr Ala
        195

<210> SEQ ID NO 10
<211> LENGTH: 408
<212> TYPE: DNA
<213> ORGANISM: Homo sapiens

<400> SEQUENCE: 10
atggctaatt acaagaagcc caaactcctc tactgtagca acgggggcca cttcctgagg      60
```

-continued

```
atccttccgg atggcacagt ggatgggaca agggacagga gcgaccagca cattcagctg    120
cagctcagtg cggaaagcgt gggggaggtg tatataaaga gtaccgagac tggccagtac    180
ttggccatgg acaccgacgg gcttttatac ggctcacaga caccaaatga ggaatgtttg    240
ttcctggaaa ggctggagga gaaccattac aacacctata tatccaagaa gcatgcagag    300
aagaattggt tgttggcct caagaagaat gggagctgca acgcggtcc tcggactcac      360 tatggccaga aagcaatctt gtttctcccc ctgccagtct cttctgat                 408
```

<210> SEQ ID NO 11
<211> LENGTH: 663
<212> TYPE: DNA
<213> ORGANISM: Artificial
<220> FEATURE:
<223> OTHER INFORMATION: synthetic DNA

<400> SEQUENCE: 11

```
atggccccg cccgtctgtt cgcgctgctg ctgttcttcg taggcggagt cgccgagtcg     60
atccgagaga ctgaggtcat cgaccccag gacctcctag aaggccgata cttctccgga    120
gccctaccag acgatgagga tgtagtgggg cccgggcagg aatctgatga ctttgagctg    180
tctggctctg gagatctgga tgacttggaa gactccatga tcggccctga agttgtccat    240
cccttggtgc ctctagatgc taattacaag aagcccaaac tcctctactg tagcaacggg    300
ggccacttcc tgaggatcct tccggatggc acagtggatg ggacaaggga caggagcgac    360
cagcacattc agctgcagct cagtgcgaaa agcgtggggg aggtgtatat aaagagtacc    420
gagactggcc agtacttggc catggacacc gacgggcttt tatacggctc acagacacca    480
aatgaggaat gtttgttcct ggaaaggctg gaggagaacc attacaacac ctatatatcc    540
aagaagcatg cagagaagaa ttggtttgtt ggcctcaaga gaatgggag ctgcaaacgc     600 ggtcctcgga ctcactatgg ccagaaagca atcttgtttc tccccctgcc agtctcttct    660
gat                                                                  663
```

<210> SEQ ID NO 12
<211> LENGTH: 221
<212> TYPE: PRT
<213> ORGANISM: Artificial
<220> FEATURE:
<223> OTHER INFORMATION: chimeric molecule

<400> SEQUENCE: 12

```
Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Ala Asn Tyr Lys Lys Pro Lys Leu Leu Tyr
                85                  90                  95

Cys Ser Asn Gly Gly His Phe Leu Arg Ile Leu Pro Asp Gly Thr Val
            100                 105                 110

Asp Gly Thr Arg Asp Arg Ser Asp Gln His Ile Gln Leu Gln Leu Ser
        115                 120                 125
```

```
Ala Glu Ser Val Gly Glu Val Tyr Ile Lys Ser Thr Glu Thr Gly Gln
    130                 135                 140

Tyr Leu Ala Met Asp Thr Asp Gly Leu Leu Tyr Gly Ser Gln Thr Pro
145                 150                 155                 160

Asn Glu Glu Cys Leu Phe Leu Glu Arg Leu Glu Asn His Tyr Asn
                165                 170                 175

Thr Tyr Ile Ser Lys Lys His Ala Glu Lys Asn Trp Phe Val Gly Leu
            180                 185                 190

Lys Lys Asn Gly Ser Cys Lys Arg Gly Pro Arg Thr His Tyr Gly Gln
        195                 200                 205

Lys Ala Ile Leu Phe Leu Pro Leu Pro Val Ser Ser Asp
210                 215                 220

<210> SEQ ID NO 13
<211> LENGTH: 144
<212> TYPE: DNA
<213> ORGANISM: Homo sapiens

<400> SEQUENCE: 13
atggcccccg cccgtctgtt cgcgctgctg ctgttcttcg taggcggagt cgccgagtcg      60
atccgagaga ctgaggtcat cgaccccag gacctcctag aaggccgata cttctccgga     120
gccctaccag acgatgagga tgta                                            144

<210> SEQ ID NO 14
<211> LENGTH: 594
<212> TYPE: DNA
<213> ORGANISM: Homo sapiens

<400> SEQUENCE: 14
atggcccccg cccgtctgtt cgcgctgctg ctgttcttcg taggcggagt cgccgagtcg      60
atccgagaga ctgaggtcat cgaccccag gacctcctag aaggccgata cttctccgga     120
gccctaccag acgatgagga tgtagtgggg cccgggcagg aatctgatga ctttgagctg    180
tctggctctg gagatctgga tgacttggaa gactccatga tcggccctga agttgtccat    240
cccttggtgc tctagataa ccatatccct gagagggcag ggtctgggag ccaagtcccc     300
accgaaccca gaaaactaga ggagaatgag gttatcccca agagaatctc acccgttgaa    360
gagagtgagg atgtgtccaa caaggtgtca atgtccagca ctgtgcaggg cagcaacatc    420
tttgagagaa cggaggtcct ggcagctctg attgtgggtg gcatcgtggg catcctcttt    480
gccgtcttcc tgatcctact gctcatgtac cgtatgaaga gaaggatga aggcagctat    540 gacctgggca gaaacccat ctacaagaaa gcccccacca tgagttcta cgcg           594

<210> SEQ ID NO 15
<211> LENGTH: 30
<212> TYPE: DNA
<213> ORGANISM: Artificial
<220> FEATURE:
<223> OTHER INFORMATION: synthetic DNA

<400> SEQUENCE: 15
ttgtcgaccc accatggccc ccgcccgtct                                       30

<210> SEQ ID NO 16
<211> LENGTH: 26
<212> TYPE: DNA
<213> ORGANISM: Artificial
<220> FEATURE:
```

```
<223> OTHER INFORMATION: synthetic DNA

<400> SEQUENCE: 16
ttgatatcta gaggcaccaa gggatg                                              26

<210> SEQ ID NO 17
<211> LENGTH: 35
<212> TYPE: DNA
<213> ORGANISM: Artificial
<220> FEATURE:
<223> OTHER INFORMATION: synthetic DNA

<400> SEQUENCE: 17
gcgtcgacag cgctaattac aagaagccca aactc                                    35

<210> SEQ ID NO 18
<211> LENGTH: 33
<212> TYPE: DNA
<213> ORGANISM: Artificial
<220> FEATURE:
<223> OTHER INFORMATION: synthetic DNA

<400> SEQUENCE: 18
ccgaattcga attctttaat cagaagagac tgg                                      33
```